(12) United States Patent
Bepler

(10) Patent No.: US 7,351,530 B1
(45) Date of Patent: Apr. 1, 2008

(54) PROGNOSTIC SIGNIFICANCE OF MOLECULAR GENETIC ABERRATIONS ON CHROMOSOME SEGMENT 11P15.5 IN NON-SMALL-CELL LUNG CANCER

(75) Inventor: Gerold Bepler, Tampa, FL (US)

(73) Assignee: Health Research, Inc., Buffalo, NY (US)

( * ) Notice: Subject to any disclaimer, the term of this patent is extended or adjusted under 35 U.S.C. 154(b) by 776 days.

(21) Appl. No.: 10/326,483

(22) Filed: Dec. 20, 2002

Related U.S. Application Data

(60) Provisional application No. 60/342,224, filed on Dec. 20, 2001.

(51) Int. Cl.
*C12Q 11/68* (2006.01)
*C12P 19/34* (2006.01)
*G01N 33/50* (2006.01)

(52) U.S. Cl. .......................... 435/6; 435/91.2; 436/64; 436/94

(58) Field of Classification Search ...................... None
See application file for complete search history.

(56) References Cited

U.S. PATENT DOCUMENTS 6,183,954 B1 * 2/2001 Bar-Shavit ...................... 435/6

OTHER PUBLICATIONS

Kim et al (Int Journal of Cancer, 2000, vol. 87, pp. 61-67).*
Abstract of Fong et al (Genes, Chromsomes and Cancer, 1994, vol. 10, pp. 183-189).*
Rosell et al (Current Opinion in Oncology, Mar. 2001, vol. 13, pp. 101-109.*
Ginsberg et al, 'Non-Small Cell Lung Cancer', In: Cancer: Principles and Practice of Oncology, 1997, DeVita et al, Ed.s, pp. 877 and 888.*
Fong et al (Genes, Chromosomes and Cancer, 1994, vol. 10, pp. 183-189).*
MOUNTAIN, *Revisions in the International System for Staging Lung Cancer*, CHEST The Cardiopulmonary and Critical Care Journal, pp. 1710-1717, downloaded from www.chestjournal.org by on Feb. 21, 2006.
Bepler et al., *Three Tumor-Suppressor Regions on Chromosome 11p Identified by High-Resolution Deletion Mapping in Human Non-Small-Cell Lung Cancer*, Proc. Natl. Acad. Sci., USA, Jun. 1994, vol. 91. pp. 5513-5517.
Bepler et al., *A 1.4-Mb High-Resolution Physical Map and Contig of Chromosome Segment 11p15.5 and Genes in the LOH11A Metastasis Suppressor Region*, Genomics, 1999, vol. 55, pp. 164-175.
Cavenee et al., *Expression of Recessive Alleles by Chromosomal Mechanisms in Retinoblastoma*, Nature, 1983, vol. 305, pp. 779-784.
Fong et al., *Tumor Progression and Loss of Heterozygosity at 5q and 18q in Non-Small Cell Lung Cancer*, Cancer Research, Jan. 15, 1995, vol. 55, pp. 220-223.
Pitterle et al., *Lung Cancer and the Human Gene for Ribonucleotide Reductase Subunit M1(RRM1)*, Mammalian Genome, 1999, vol. 10, pp. 916-922.
Tran et al., *High-Density Marker Analysis of 11p15.5 in Non-Small Cell Lung Carcinomas Reveals Allelic Deletion of One Shared and One Distinct Region When Compared to Breast Carcinomas*, Cancer Research, Jul. 1, 1996, vol. 56, pp. 2916-2921.
Weston et al., *Differential DNA Sequence Deletions from Chromosomes 3, 11, 13, and 17 in Squamous-Cell Carcinoma, Large-Cell Carcinoma, and Adenocarcinoma of the Human Lung*, Proc. Natl. Acad. Sci, USA, Jul. 1989, vol. 86, pp. 5099-5103.
Zhao et al., *Transcript Map and Complete Genomic Sequence for the 310 kb Region of Minimal Allele Loss on Chromosome Segment 11p15.5 in Non-Small-Cell Lung Cancer*, Oncogene, 2001, vol. 20, pp. 8154-8164.

* cited by examiner

*Primary Examiner*—Karen A. Canella
(74) *Attorney, Agent, or Firm*—Hodgson Russ LLP

(57) ABSTRACT

The present invention provides a method for detection of loss of heterozygosity (LOH) at human chromosome segment 11p15.5 in a tumor sample from a patient with non-small-cell lung cancer (NSCLC), and a method for prognosis of the patient's disease progression. The prognosis is useful for determining the course of treatment following surgical resection of tumor.

7 Claims, 5 Drawing Sheets

PROGNOSTIC SIGNIFICANCE OF MOLECULAR GENETIC ABERRATIONS ON CHROMOSOME SEGMENT 11P15.5 IN NON-SMALL-CELL LUNG CANCER

This application claims priority to U.S. Provisional Patent Application with Ser. No. 60/342,224, filed Dec. 20, 2001, the disclosure of which is incorporated by reference This work was supported by grants from the National Cancer Institute (5RO1 CA 70317 and 5P01 CA 72099). The government has certain rights in the invention.

FIELD OF THE INVENTION

The present invention relates to methods useful for prognosticating cancer patients' survival in relation to chromosomal stability.

BACKGROUND OF THE INVENTION

It is estimated that 169,500 patients were diagnosed with lung cancer in the United States in 2001, and 157,400 died as a result of the disease. Lung cancer causes more death than colorectal cancer, breast cancer and prostate cancer combined. (1) Five-year survival rates have improved from 8% in the early 1960's to 15% in the early 1990's. This doubling of the 5-year lung cancer survival rate is encouraging and has resulted in a shift from the previous nihilism associated with lung cancer treatment to a guarded optimism regarding outcome from treatment. Although locoregional control of non-small-cell lung cancer (NSCLC) can be achieved by surgery and radiation, more than 70% of relapses in patients with stage I disease occur at distant sites. (2) Thus, most patients with NSCLC must have systemic disease, even at the earliest stages. Efforts at improving the management and outcome of patients with this disease are evolving. Recent efforts have been directed at chemoprevention to reduce incidence and at neoadjuvant and adjuvant chemotherapy to reduce the high systemic relapse rate.

Cytotoxic intervention strategies have associated toxicities, particularly in this target population where rates of comorbidities from atherosclerotic disease and chronic benign lung disease are high. Directing treatment strategies toward patients with NSCLC most likely to benefit has been guided by clinical variables such as disease stage, performance status, and weight loss. Other pathologic and molecular variables include submicroscopic metastases, (3) metabolic activity by imaging, (4) expression of proteins in various pathways regulating cellular growth and differentiation, (5-7) mutations in oncogenes and tumor suppressor genes, (8-12) expression of extracellular matrix proteinases and markers of angiogenesis, (13-15) and genome instability.

The predominant type of genome instability in cancer is structural aberration of chromosomes, i.e., deletions, translocations, and insertions. These are thought to arise as a result of impaired repair of DNA double-strand breaks by homologous recombination and non-homologous end joining. (16,17) Loss of heterozygosity (LOH) analysis is the most frequently used technique to assess genome instability, and allele loss often heralds the discovery of genes with key functions in tumor development and progression. (18)

Prior to the present invention, few investigations have shown significant associations between LOH and survival of patients with lung cancer. LOH (4/40) at chromosome segment 11p13 was predictive of poor outcome in squamous cell carcinomas with a p-value of 0.02, (20) and LOH (21/66) for the HRAS locus near the telomere of 11p was predictive of poor outcome for all histopathologic subtypes with a p-value of 0.04. (25) However, Sanches-Cespedes et al. did not find such an association despite comparable numbers of cases studied and similar frequencies of LOH (12/63 for 11p13 and 19/61 for the HRAS locus). (26) Three regions of LOH on chromosome 3p, namely 3p14, 3p21, 3p25-26, have been investigated for associations with survival. In one study of 110 patients with NSCLC, LOH was found in 45 of 98 informative cases, and there was a trend towards poor survival (p=0.0631). (27) A second study with 35 patients in pathologic stage I showed no trend towards poor survival, (24) as did a third study with 103 patients. (28) The APC/MCC tumor suppressor gene is located on segment 5q21. LOH was significantly correlated with poor survival (p=0.01, LOH in 22/75 NSCLCs) in one study (40) but not in a second study (p=0.33, 14/68 NSCLCs). (26) These results suggest that LOH per se, as a marker of chromosomal instability resulting from impaired repair of DNA double-strand breaks, does not appear to be prognostically useful. Thus, there is a need for identifying loci wherein the presence of LOH could be reliably used for prognosis.

SUMMARY OF THE INVENTION

The present invention provides a method for detection of loss of heterozygosity (LOH) at human chromosome segment 11p15.5. The present invention also provides a method for prognosis in an individual with NSCLC. The method comprises detecting LOH in the 11p15.5 region. The presence of LOH is indicative of poor prognosis in the NSCLC patient. This is useful for treatment decisions following surgical resection.

DETAILED DESCRIPTION OF THE INVENTION

The terms "loss of heterozygosity" or "LOH" as used herein mean the chromosomal condition wherein one of a pair of heterozygous alleles is lost due to a deletion of DNA from one of the paired chromosomes on which the allele is located leaving only the remaining allele to be expressed and the affected cells functionally homozygous at the gene locus where the deletion occurred.

The present invention provides a method for detecting LOH at human chromosome segment 11p15.5 in a non-small-cell lung cancer (NSCLC) patient. The presence of LOH is used to determine the patient's prognosis and to recommend a course of treatment.

Figure 1:
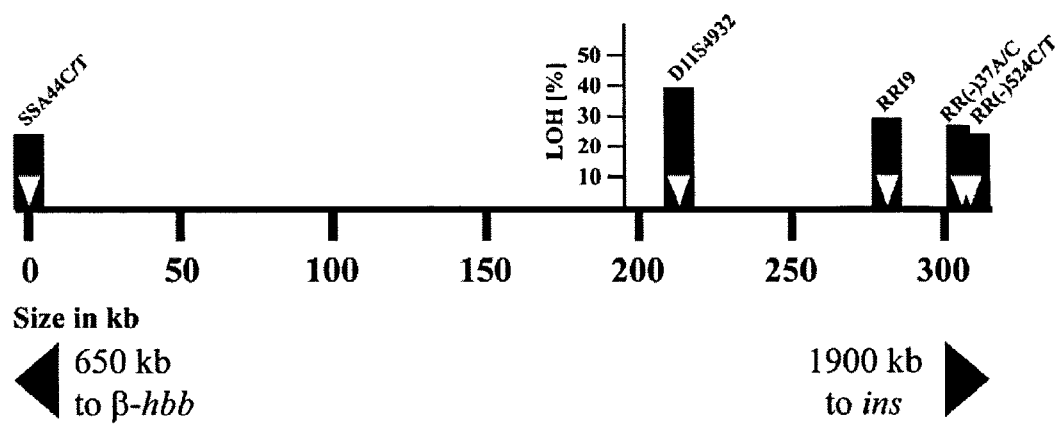
FIG. 1. Schematic representation of the region located on chromosome segment 11p15.5 between the beta-hemoglobin (β-hbb) and insulin (ins) genes. The scale provides physical distances in kilobase-pairs (kb). Arrows indicate the exact position of the five polymorphic markers used. The bars depict the frequency of LOH.

The centromeric part of human chromosome segment 11p15.5 includes region LOH11A. We investigated the frequency and clinical significance of LOH for this region by studying 5 polymorphic markers in 193 patients with pathological stage I and II disease who underwent resection for NSCLC. These 5 markers (22) are distributed over 310 kb and cover the smallest area of common allele loss (FIG. 1). The data indicate a correlation between the presence of LOH and a non-favorable prognosis.

The statistically significant association with survival for stage I disease parallels the finding of LOH on chromosome 18q in stage B (stage II) colon cancer. (29) In this disease, patients with stage B and LOH at 18q have a prognosis similar to patients with stage C (stage III). Adjuvant systemic cytotoxic therapy is not routinely used in stage B patients with colon cancer because of marginal benefit. This is in contrast to patients with stage C disease, where adjuvant therapy resulted in a 33% relative reduction and 16% absolute reduction of mortality at 42 months. (30) As a result, this molecular marker is often used to guide the decision on adjuvant chemotherapy use in patients with stage B colon cancer. At the present time, adjuvant or neoadjuvant chemotherapy for patients with completely resected stage I or stage II NSCLC is not recommended. (31) However, because of the extraordinary high systemic relapse rate and low 5-year survival rate multiple adjuvant and neoadjuvant phase II and phase III clinical trials are currently being conducted. Thus, the methods of the present invention can be used as a powerful prognostic discriminator and thus are useful to help recommend a course of treatment for NSCLC patients, such as which patients should or should not receive systemic treatment in addition to surgical resection.

Different techniques for detection of LOH have been developed. Through the use of DNA probes, DNA from an individual's normal cells can be compared with DNA extracted from the same individual's tumor cells and LOH can be identified using experimental techniques known in the art.

One means of testing for loss of an allele is by digesting the DNA sample and a known heterozygous DNA sample with a restriction endonuclease. Restriction endonucleases are well known in the art for their ability to cleave DNA at specific sequences, and thus generate a discrete set of DNA fragments from each DNA sample. The restriction fragments of each DNA sample can be separated by any means known in the art. For example, agarose or polyacrylamide gel electrophoresis can be used to electrophoretically separate fragments according to physical properties such as size. The restriction fragments can then be hybridized to nucleic acid probes which detect restriction fragment length polymorphisms (RFLPs).

Another means for detecting the presence of allelic deletions is by amplifying the DNA from the patients normal and tumor tissue. Amplification may be accomplished by methods known to those skilled in the art such as polymerase chain reaction (PCR), ligation amplification (or ligase chain reaction, LCR) and amplification methods based on the use of Q-beta replicase. (See, e.g., U.S. Pat. Nos. 4,683,195 and 4,683,202 and Innis (1990) for PCR, and Wu (1989) for LCR.) Another means for detecting LOH is by global DNA amplification followed by an allele specific hybridization to oligonucleotide probes, optionally on a chip.

In one embodiment, the method of the present invention comprises amplifying DNA from a tumor tissue sample from an individual with NSCLC using primers specific to the 11p15.5 region and comparing the amplification to an amplification from a normal tissue sample from the same individual. A difference between the tumor sample and the normal sample is considered to be an indication of LOH in the 11p15.5 region. The LOH is used for prognostic purposes and/or to determine a course of subsequent treatment for the individual.

Tissue samples may be obtained from NSCLC patients with standard methods known to those skilled in the art, such as biopsies, surgical resections, or the like. The tissue sample may be taken from the patient directly or from a sample previously removed from the patient, such as a tumor. The tissue sample may also be in a preserved state, such as by being embedded in paraffin. Samples of non-cancerous tissue may be taken from the patients to be used as standards for making LOH determinations or measurements. DNA from peripheral blood mononuclear cells or tumor-free lymph nodes collected during pathologic staging can serve as a source for germline DNA and can be used initially to assess if a patient's allelotype is suitable for LOH analysis.

Extracting DNA from the tissue sample may be performed in a variety of ways known to those skilled in the art. For example, the tissue sample may be pulverized in liquid nitrogen and the DNA extracted using any of several commercially available kits designed for this purpose. Alternatively, the tissue sample may be incubated with protease enzymes in the presence of surfactants to release DNA and to degrade proteins that can interfere in nucleic acid amplification. Other subsequent steps in purification of extracted DNA may include treatment with RNAase to remove contaminating RNA, followed by DNA precipitation with a solvent such as ethanol or a mixture of solvents such as phenol and isoamyl alcohol to remove protein and other cellular material, followed by DNA hydration. In the case of paraffin-embedded tissues, paraffin is usually removed by extraction with solvents such as xylene in a multiple step procedure prior to a proteinase treatment. For a general description of DNA extraction from tissue samples, see Sambrook J, Fritsch E F, Maniatis T, (1989) Molecular Cloning; A Laboratory Manual, 2nd ed. Cold Spring Harbor Laboratory Press, New York.

In one embodiment, the method of the present invention comprises the use of PCR to amplify the 11p15.5 region of human chromosome segment 11p15.5 in conjunction with primers described herein. PCR reaction conditions and modifications thereof can be found in PCR Protocols: A Guide To Methods And Applications, Academic Press, San Diego, Calif. (1990). PCR results in amplification of target DNA through repeated cycles of double stranded DNA denaturation, oligonucleotide primer annealing and primer extension. The PCR primers may be end-labeled with a radionucleotide such as gamma-[$^{33}$P]-ATP according to standard methods. The PCR products may be digested with restriction enzymes according to methods known to those skilled in the art. For a description of restriction digestion protocols, see Sambrook J, Fritsch E F, Maniatis T, (1989) Molecular Cloning; A Laboratory Manual, 2nd ed. Cold Spring Harbor Laboratory Press, New York. Examples of suitable restriction enzymes include but are not limited to HinfI, MspI, SacI, BbsI, and ApoI.

Whole and restriction digested PCR products may be analyzed by their eletrophoretic migration profiles during gel electrophoresis according to methods known to those skilled in the art and as described above. Whole and restriction digested PCR products separated by gel electophoresis may also be analyzed using traditional techniques such as Southern blotting or analyzed with phosphorimager systems or separated on a WAVE® DNA fragment analysis system. Using the analytic methods described herein, ratios of amplification products can be quantified and a measure of LOH obtained.

By using commercially available statistical software packages, the data from the analysis of PCR products and restriction digests thereof can be correlated to the prognosis of the patients from whom the samples were taken. An example of such a statistical analysis is Cox regression analysis. An example of software suitable for carrying out such an analysis is the SPSS10.07 software package (Statistical Package for Social Science; SPSS Inc., Chicago, Ill., June 2000). By obtaining an assessment of the LOH of a patient's tissue sample, a prognosis can be made to predict the patient's disease outcome and used to recommend a course of therapy. The presence of LOH is taken as an indicator of poor prognosis whereas the absence of LOH is taken as an indicator of favorable prognosis. The prognosis can be determined by statistical analysis of the LOH assessment. The following example is presented for illustrating the invention and is not intended to be restrictive.

EXAMPLE I

Specimen Collection and DNA Extraction. Paired tumor/normal specimens were obtained from patients undergoing curative surgery for pathological stage I or stage II NSCLC as part of an Institutional Review Board-approved research study from February 1985 to July 1996. Specimens were pulverized in liquid nitrogen, and DNA was extracted (Qiagen, Valencia, Calif.).

Data Collection. Demographic and clinical data were collected by chart review, telephone contact, or query of the social security death index. For each patient these included the dates of birth, diagnosis, sample collection, relapse, and death or last follow-up; tumor histology and grade of differentiation; pathologic disease stage according to the American Thoracic Society (ATS) staging system, (22) performance status using the Eastern Cooperative Oncology Group (ECOG) scale ("0", no symptoms; "1", minor symptoms; "2", symptoms present, out of bed or chair for more than 50% of the waking hours); weight loss (more or less than 5% in the 3 months preceding diagnosis); gender and place of residence; and quantity of cigarette use over lifetime and current smoking status. Patients who smoked less than 100 cigarettes in their lifetime were classified as non-smokers. (23)

Allele Loss Analysis. The five polymorphic markers analyzed for LOH were restriction site polymorphisms. DNA was amplified with primer pairs (SEQ ID NOs: 1-10, Table 1) flanking the polymorphic site followed by restriction enzyme digestion. Details on the polymorphic loci are provided in Table 1. The primers used were as follows:

TABLE 1

Characteristics of Polymorphic Markers

| Loci | Forward Primer (5'-3') [centromeric] | Reverse Primer (5'-3') [telomeric] | Amplicon Size [bp] | Restriction Enzyme | Fragment Sizes [bp] |
|---|---|---|---|---|---|
| SSA44C/T | CCCCT TTCCT CTCAG ACTTG (SEQ ID NO:1) | ATCTA GTGGG GTTCA CTCAC CT (SEQ ID NO:2) | 103 | HinfI | 69/31 |
| D11S4932 | GACAA AGCCA AAGCT CTTTA C (SEQ ID NO:3) | CTGGA AGACA CTTTC TCAAA C (SEQ ID NO:4) | 200 | MspI | 167/31 |
| RRI9 | CCCCA AAGTC CATCA GAGAG (SEQ ID NO:5) | TCTCC CTAAT TGGCT GGATG (SEQ ID NO:6) | 492 | SacI | 262/226 |
| RR(-)37A/C | CTGCT CAGGG GAAAG AACTG (SEQ ID NO:7) | GGTCT TGCCC AGACT CAACA (SEQ ID NO:8) | 217 | BbsI | 156/57 |
| RR(-)524C/T | CTTTT AGATC GGCCA GAGGA (SEQ ID NO:9) | ATACC CTGTC TCTGC CACCA (SEQ ID NO:10) | 176 | ApoI | 102/70 |

In this assay the forward or the reverse primer of each primer pair was end labeled with gamma-[$^{33}$P]-ATP according to standard methods. PCR products were digested with restriction enzymes prior to separation for allele analysis. Digested amplicon fragments were separated on denaturing 10% polyacrylamide gels and visualized on phosphor imaging screens (Molecular Dynamics, Sunnyvale, Calif.) and/or separated on a WAVE® DNA fragment analysis system (Transgenomic, Santa Clara, Calif.). Some specimen pairs were also analyzed by Southern blotting as previously described. (19) LOH was assessed by quantification of the area of allele signals with a phosphorimager or WAVE® analyzer and scored as LOH if the calculated allele ratio was less than 0.6. WAVE® DNA fragment analysis is one of several methods for automated DNA fragment size analysis. Other methods for detecting DNA sequence variations (including single nucleotide polymorphisms) can also be used to detect LOH.

In normal tissue specimens, the ratio of signal intensities between two alleles (A1 and A2) is balanced. In tumor specimens the ratio can deviate from this normal specimen ratio for two reasons, i.e., allele loss or allelic imbalance. In case of allele loss, the ratio should be 0.0. However, tumor specimens contain varying amounts of contaminating normal cells, which result in ratios that reflect the proportion of DNA in a tumor specimen derived from normal diploid cells. Alternatively, allele ratios below 1.0 and above 0.0 could result from allelic imbalance in tumor cells, i.e., both alleles (A1 and A2) are present, but not at a 1:1 ratio. This can originate within a clonal population of cells; for instance all cells have two copies of allele A1 and one copy of allele A2 as a result of locus amplification or as a result of aneuploidy. Alternatively, allelic imbalance can result from variations of allele content in different tumor cells, i.e., tumor heterogeneity. Aneuploidy and tumor heterogeneity are unlikely mechanisms to account for the observed allele ratios because ratios for different alleles in a narrowly defined chromosomal region should be very similar.

Figure 2:
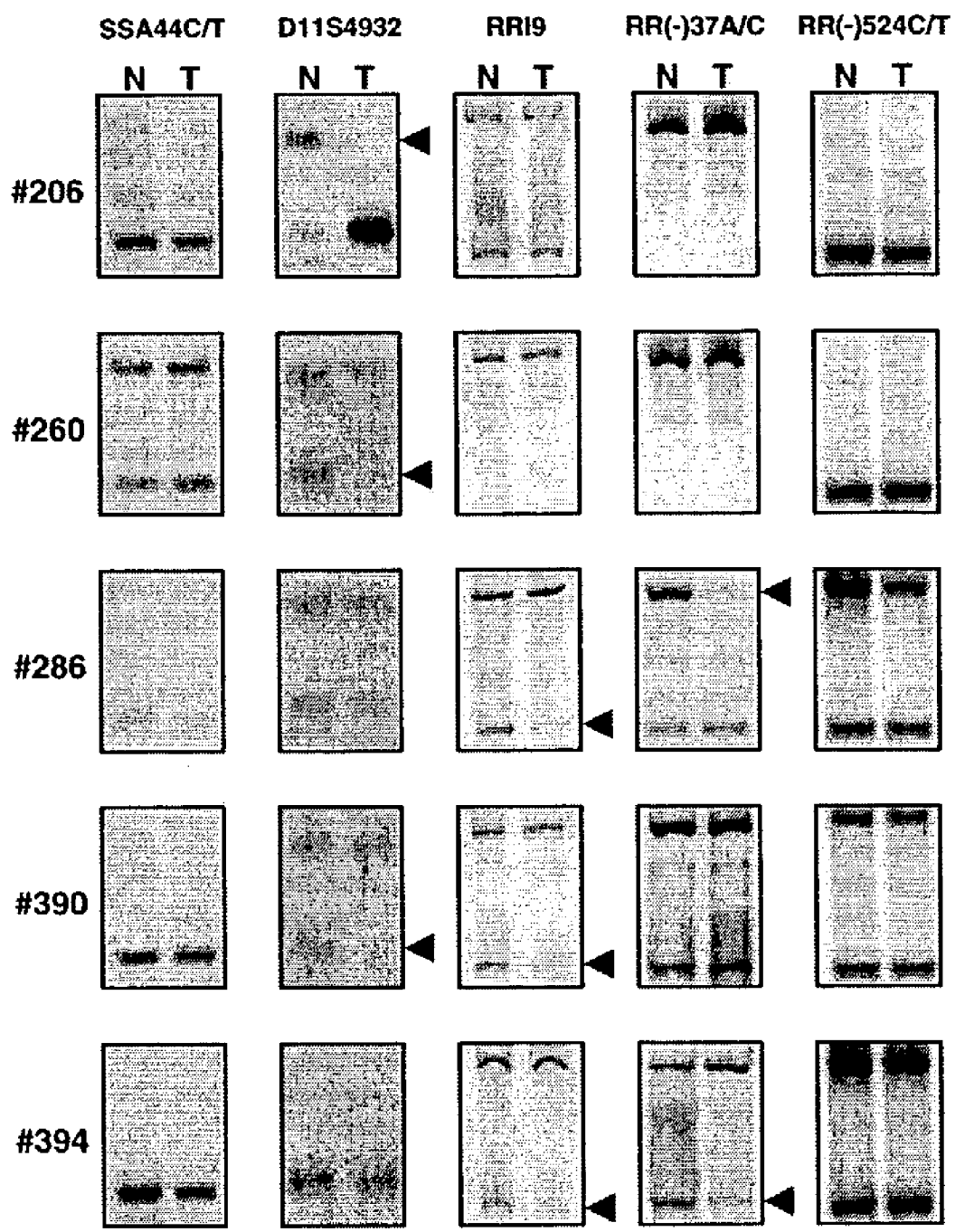
FIG. 2. Phosphorimages of tumor pairs analyzed for the markers SSA44C/T, D11S4932, RRI9, RR(−)37A/C, and RR(−)524C/T. "N" indicates DNA from normal tissue and "T" DNA from tumor tissue. Arrows point to lost alleles.

As shown in FIG. 2, allele ratios were mainly close to 1.0 for one set of alleles and significantly different for other sets of alleles, which strongly favors allele loss (and contamination with normal DNA) as the underlying cause of allelic differences. Locus amplification could also explain the results. We used an allele ratio of 0.6 as a cut-off for LOH because we had previously determined that the $5^{th}$, $10^{th}$, and $25^{th}$ percentile of signal intensity ratios among normal specimens from different individuals were 0.6, 0.7, and 0.8 respectively.

Statistical Analysis. The primary, analytical, statistical method to assess the association between LOH (absent, present, indeterminate) and survival while controlling for potential confounders was a Cox regression analysis. The SPSS10.07 software was used (Statistical Package for Social Science; SPSS Inc., Chicago, Ill., June 2000). The confounders in the adjusted model included disease stage (I, II), ECOG performance status (0, 1, 2), weight loss (present, absent), gender (male, female), age (more or less than the median), and smoking status (never smoker, smokers with more and those with equal or less than the median measured in number of packs smoked per day multiplied by the number of years, i.e., PY). Unadjusted Cox regression analyses were done with each predictor variable entered singly into the model. The proportional hazards assumption was verified in all analyses.

Characteristics of Lung Cancer Patients. Paired DNA specimens for analysis were available on 193 patients. The study population included 52 women and 141 men. The average age was 63.2 years (median 64.2 years) with a range of 35.0 to 81.9 years. Fifteen patients were non-smokers, and 165 were smokers or former smokers (median number of PY was 50, average number of PY was 52.5, range 1-150). Smoking information was not available for 13 patients. Ninety-four patients had adenocarcinoma (including 15 bronchioloalveolar cell carcinomas), 77 had squamous cell carcinoma, 9 had large cell carcinoma, and 13 had adenosquamous carcinoma. The distribution by disease stage was 56 stage IA, 77 stage IB, 12 stage IIA, and 48 stage IIB. For analyses, stage IA and B and stage IIA and B were combined. Table 2 provides an overview of the disease stage by histopathology.

TABLE 2

Histopathology and Pathologic Stage (N = 193)

| Stage | Adeno (N = 94) | Squamous (N = 77) | Large (N = 9) | Ad/Sq (N = 13) |
|---|---|---|---|---|
| Stage I (N = 133) | | | | |
| T1N0M0 | 32 | 21 | 3 | 0 |
| T2N0M0 | 35 | 30 | 6 | 6 |
| Stage II (N = 60) | | | | |
| T1N1M0 | 4 | 7 | 0 | 1 |
| T2N1M0 | 17 | 15 | 0 | 4 |
| T3N0M0 | 6 | 4 | 0 | 2 |

The ECOG performance status was "0" in 90 patients, "1" in 76, "2" in 13, and unknown in 14. Weight loss at the time of diagnosis was present in 22 patients, absent in 153, and unknown in 18. Eighty-seven patients were deceased and 106 were alive, and survival or follow-up time ranged from less than 1 month to 164.5 months. Four patients, all with stage II disease, died within 30 days of surgery, and they were included in the analysis.

LOH Analysis.

The observed heterozygosity rates for the five polymorphic markers ranged from 25.9% to 42.9% (table 3).

TABLE 3

Heterozygosity and LOH for Individual Markers

| Markers | Not Evaluable [N] | Homozygous [N] | Heterozygous [N] | Heterozygosity [%] | LOH [N] | LOH [%] |
|---|---|---|---|---|---|---|
| SSA44C/T | 8 | 137 | 48 | 25.9 | 12 | 25.0 |
| D11S4932 | 4 | 136 | 53 | 28.0 | 21 | 39.6 |
| RRI9 | 18 | 100 | 75 | 42.9 | 22 | 29.3 |
| RR(−)37A/C | 11 | 114 | 68 | 37.4 | 19 | 27.9 |
| RR(−)524C/T | 16 | 101 | 76 | 42.9 | 19 | 25.0 |

Figure 3:
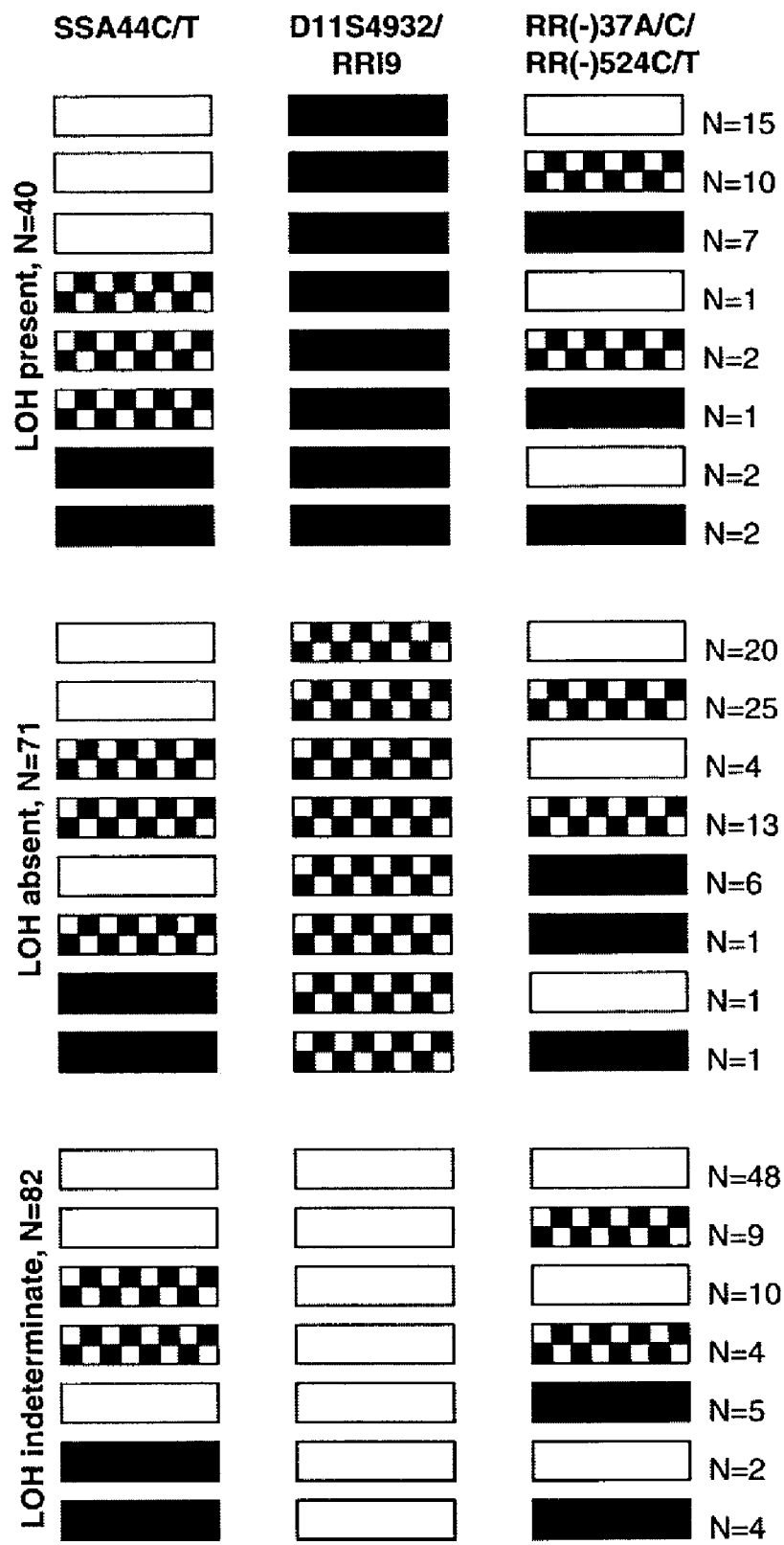
FIG. 3. The patterns of allelic loss for all 193 lung cancer cases is shown. A checkered box symbolizes retained heterozygosity, a solid black box symbolizes LOH, and a solid white box symbolizes homozygosity.

LOH for these markers was found in 25.0% (SSA44C/T), 39.6% (D11S4932), 29.3% (RRI9), 27.9% (RR(−)37A/C), and 25.0% (RR(−)524C/7) of patients and is illustrated in Table 3. FIG. 2 depicts five examples of observed LOH patterns and shows that the region with highest frequency of LOH is located in the center of the region including D11S4932 centromeric and RRI9 telomeric. In the 111 cases heterozygous for D11S4932, RRI9, or both, LOH was found in 40 (36.0%). Of the 82 cases that were uninformative for D11S4932 and RRI9, 11 had LOH for at least one of the other three markers (SSA44C/T and/or RR(−)37A/C, or SSA44C/T and/or RR(−)524C/T if RR(−)37A/C was uninformative). In addition, 9 cases heterozygous without LOH for either D11S4932 or RRI9 had LOH for one of the other markers. The number of cases with a specific allelic pattern is shown in FIG. 3.

Prognostic Significance of LOH at 11p15.5.

For the LOH variable (present, absent, indeterminate), patients were divided into three groups. One group (N=40) contained patients with LOH for D11S4932, RRI9, or both markers. The second group (N=71) contained patients without allele loss, i.e., retained heterozygosity for these markers. The last group (N=82) contained patients with unknown LOH status (both markers, D11S4932 and RRI9, were uninformative). Using the Chi-square test of independence, we did not find a statistically significant association between the categorical variables disease stage, performance status, weight loss, gender, age, smoking status, and LOH.

Figure 4:
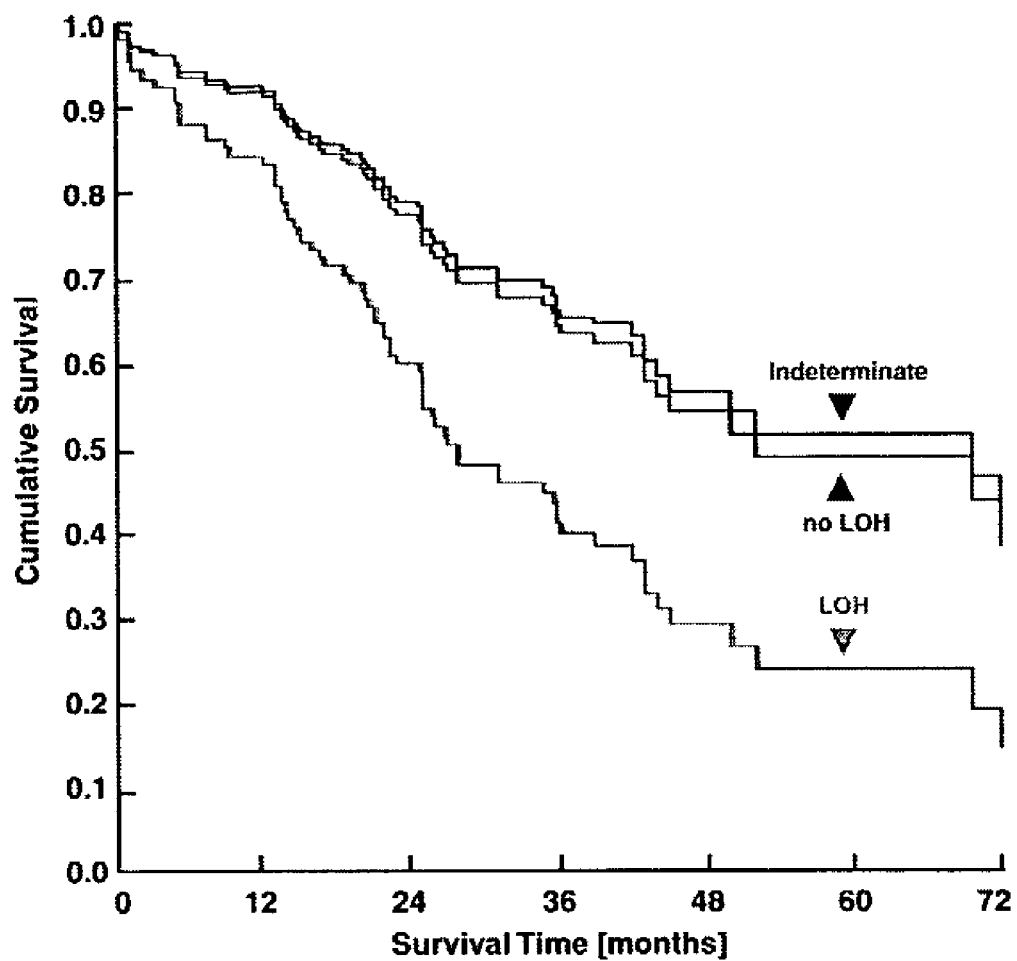
FIG. 4. Cox regression survival curves for patients with LOH (N=40), without LOH (N=71), and with indeterminate LOH status (N=82). The survival difference between patients with and without LOH was significant at p=0.021, and it was not significantly different between patients without LOH and indeterminate LOH (p=0.819).

Table 4 and FIG. 4 display the results from the Cox regression analysis.

TABLE 5

Median Survival by LOH Status and Pathologic Tumor Stage

| | LOH Absent | | LOH Present | | LOH Indeterminate | |
|---|---|---|---|---|---|---|
| | Number of Patients | Median Survival [months] | Number of Patients | Median Survival [months] | Number of Patients | Median Survival [months] |
| Stage I | 50 | 36.0 | 26 | 24.9 | 57 | 37.6 |
| Stage II | 21 | 25.1 | 14 | 18.5 | 25 | 21.1 |

TABLE 4

Cox Proportional Hazard Analysis

| | Alive [N] | Dead [N] | Median Survival [months] | Adjusted Relative Risk* | Adjusted 95% Confidence Interval | Unadjusted Relative Risk** |
|---|---|---|---|---|---|---|
| LOH | | | | | | |
| Absent | 42 | 29 | 28.0 | 1.00 | Reference | 1.00 |
| Present | 11 | 29 | 22.4 | 2.01† | 1.11-3.64 | 2.12† |
| Indeterminate | 53 | 29 | 35.3 | 0.93 | 0.50-1.70 | 0.81 |
| Disease Stage | | | | | | |
| I | 79 | 54 | 35.8 | 1.00 | Reference | 1.00 |
| II | 27 | 33 | 22.0 | 1.69 | 0.97-2.94 | 1.89† |
| Performance Status | | | | | | |
| 0 | 53 | 37 | 25.5 | 1.00 | Reference | 1.00 |
| 1 | 39 | 37 | 35.1 | 1.25 | 0.73-2.12 | 1.08 |
| 2 | 6 | 7 | 53.9 | 0.70 | 0.30-1.66 | 0.84 |
| Weight Loss | | | | | | |
| Absent | 90 | 63 | 32.8 | 1.00 | Reference | 1.00 |
| Present | 7 | 15 | 22.7 | 1.67 | 0.87-3.23 | 2.10† |
| Gender | | | | | | |
| Female | 38 | 14 | 35.2 | 1.00 | Reference | 1.00 |
| Male | 68 | 73 | 26.0 | 1.98 | 0.98-3.99 | 2.10† |
| Age at Diagnosis | | | | | | |
| ≦64.2 years | 55 | 41 | 28.0 | 1.00 | Reference | 1.00 |
| >64.2 years | 151 | 46 | 28.0 | 1.35 | 0.83-2.19 | 1.10 |
| Smoking History | | | | | | |
| Never | 8 | 7 | 25.1 | 1.00 | Reference | 1.00 |
| 1-50 PY | 67 | 40 | 32.1 | 0.77 | 0.31-1.93 | 0.72 |
| >50 PY | 24 | 34 | 25.0 | 1.09 | 0.42-2.78 | 1.33 |

*Relative risks for each variable are adjusted for all other factors listed. A † indicates the p-value is less than 0.05 for comparisons to the reference category of this variable.
**Relative risks are for each variable entered singly into the model. These are unadjusted values. A † indicates the p-value is less than 0.05 for comparisons to the reference category of this variable.

Figure 5:
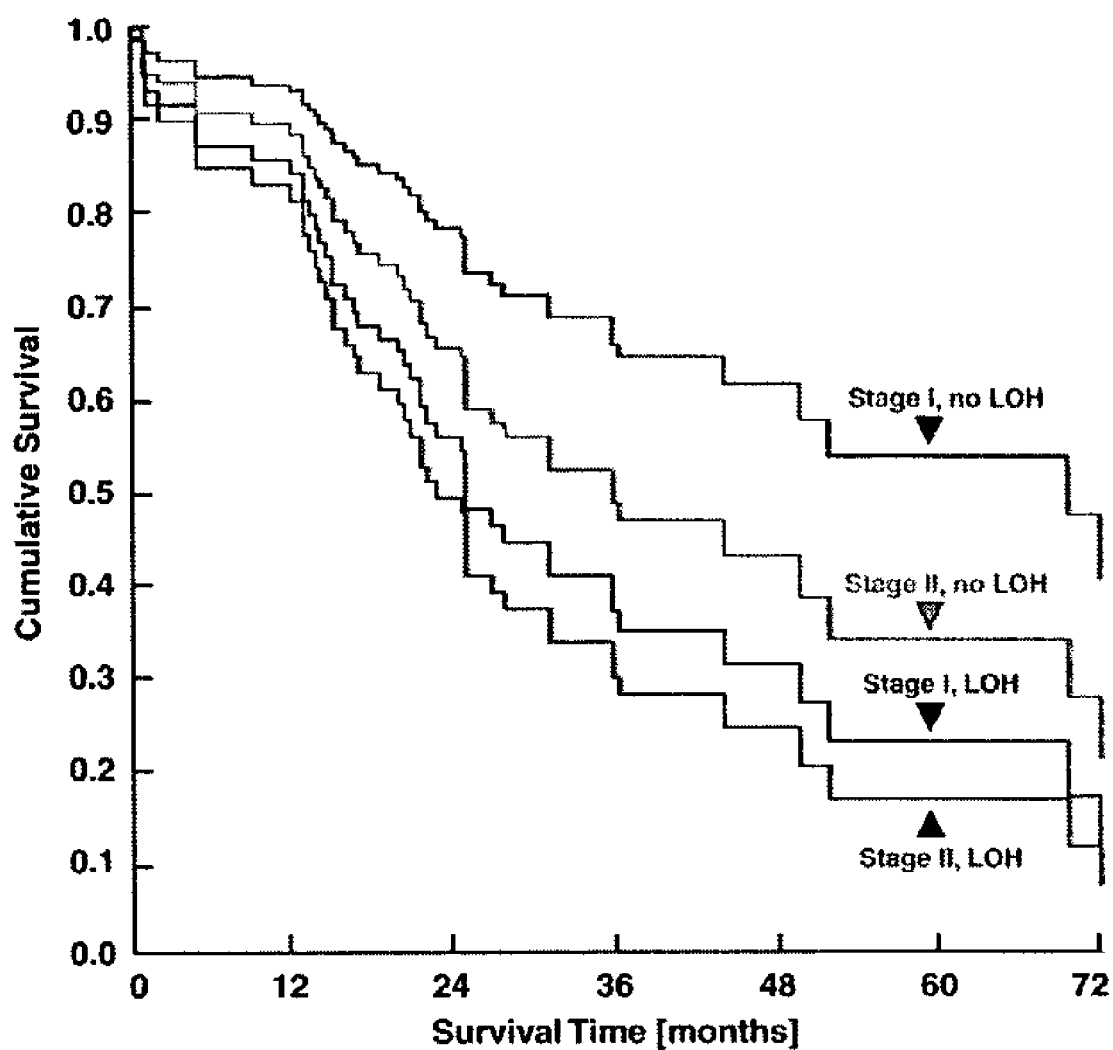
FIG. 5. Cox regression survival curves by pathologic disease stage. In stage I, patients with LOH had a relative risk of dying of 2.38 (p=0.038) compared to those without LOH, and it was comparable to that of patients with stage II disease without LOH (RR=1.67, p=0.298).

After adjusting for covariates associated with survival, patients with LOH had a significantly shorter survival than patients without LOH (RR=2.01, p=0.021). The survival of patients with indeterminate LOH status was similar to the survival of patients without LOH. Other independent predictors of survival were disease stage (p=0.064) and gender (p=0.057). The effect of LOH at 11p15.5 on survival of patients by pathologic disease stage was analyzed (see table 5), and adjusted Cox regression survival curves are present in FIG. 5. Patients with stage I and no LOH (N=50) had a significantly longer survival time compared to patients with stage I and LOH (RR=2.38, p=0.038). A similar trend towards decreased survival with allele loss was seen in Stage II patients with LOH.

We reanalyzed the data after moving the 11 patients with uninformative D11S4932 and RRI9 status but LOH for any of the adjacent markers (SSA44C/T, RR (−) 524C/T, RR(−) 37A/C) into the group of patients with LOH (last three allelic patterns shown in FIG. 3). The difference in survival between patients with and without LOH adjusted for covariates remained statistically significant (RR=1.93, p=0.029).

The methods of the present invention indicate that LOH in this region is predictive of survival. Our results indicate that allele loss in the LOH11A region on chromosome segment 11p15.5 results in at least a partial loss of function of a gene that impacts on cell proliferation and the ability of transformed cells to establish clonal growth. The p-value was 0.021 in a Cox regression analysis, which included 111 informative patients.

It should be understood that while the invention has been described in detail herein, the examples were for illustrative purposes only. Other modifications of the embodiments of the present invention that are obvious to those skilled in the art are intended to be within the scope of the appended claims.

REFERENCES

1. Greenlee R T, Hill-Harmon M B, Murray T, et al: Cancer statistics, 2001. CA Cancer J Clin 51:15-36, 2001
2. Martini N, Ginsberg R: Treatment of stage I and II disease, in Aisner J, Arriagada R, Green M, et al (eds): Comprehensive textbook of thoracic oncology. Baltimore, Williams and Williams, 1996, pp 339-350
3. Pantel K, Izbicki J, Passlick B, et al: Frequency and prognostic significance of isolated tumour cells in bone marrow of patients with non-small cell lung cancer without overt metastases. Lancet 347:649-653, 1996
4. Vansteenkiste J, Stroobants S, Dupont P, et al: Prognostic importance of the standardized uptake value on $^{18}$F-fluoro-2-deoxy-glucose-positron emission tomography scan in non-small-cell lung cancer: an analysis of 125 cases. J Clin Oncol 17:3201-3206, 1999
5. Greatens T, Niehans G, Rubins J, et al: Do molecular markers predict survival in non-small-cell lung cancer. Am J Respir Crit Care Med 157:1093-1097, 1998
6. Graziano S, Kern J, Herndon J, et al: Analysis of neuroendocrine markers, HER2 and CEA before and after chemotherapy in patients with stage IIIA non-small cell lung cancer: a Cancer And Leukemia Group B study. Lung Cancer 21:203-211, 1998
7. Ramnath N, Hernandez F J, Tan D T, et al: MCM2 is an independent predictor of survival in patients with non-small-cell lung cancer. J Clin Oncol 19: in press, 2001
8. Slebos R J, Hruban R H, Dalsio O, et al: Relationship between K-ras oncogene activation and smoking in adenocarcinoma of the human lung. J Natl Cancer Inst 83:1024-1027, 1991
9. Carbone D, Mitsudomi T, Chiba I, et al: p53 immunostaining positivity is associated with reduced survival and is imperfectly correlated with gene mutations in resected non-small cell lung cancer. A preliminary report of LCSG 871. Chest 106 (suppl):377S-381S, 1994
10. Fukuyama Y, Mitsudomi T, Sugio K, et al: K-ras and p53 mutations are an independent unfavourable prognostic indicator in patients with non-small-cell lung cancer. Br J Cancer 75:1125-1130, 1997
11. Brambilla E, Moro D, Gazzeri S, et al: Alterations of expression of rb, p16(INK4A) and cyclin D1 in non-small cell lung carcinoma and their clinical significance. J Pathol 188:351-360, 1999
12. Schiller J H, Adak S, Feins R H, et al: Lack of prognostic significance of p53 and K-ras mutations in primary resected non-small cell lung cancer on E4592: a laboratory ancillary study on an Eastern Cooperative Oncology Group prospective randomized trial of postoperative adjuvant therapy. J Clin Oncol 19:448-457, 2001
13. Harpole D, Richards W, Herndon J, et al: Angiogenesis and molecular biologic sub-staging in patients with stage I non-small cell lung cancer. Ann Thorac Surg 61:1470-1476, 1996
14. Robert C, Bolon I, Gazzeri S, et al: Expression of plasminogen activator inhibitors 1 and 2 in lung cancer and their role in tumor progression. Clin Cancer Res 5:2094-2102, 1999
15. Yuan A, Y u C J, Kuo S H, et al: Vascular edothelial growth factor 189 MRNA isoform expression specifically correlates with tumor angiogenesis, patient survival, and postoperative relapse in non-small-cell lung cancer. J Clin Oncol 19:432-441, 2001
16. Rouet P, Smith F, Jasin M: Introduction of double-strand breaks into the genome of mouse cells by expression of a rare-cutting endonuclease. Mol Cell Biol 14:8096-8106, 1994
17. Liang F, Han M, Romanienko P, et al: Homology-directed repair is a major double-strand break repair pathway in mammalian cells. Proc Natl Acad Sci USA 95:5172-5177, 1998
18. Cavenee W K, Dryja T P, Phillips R A, et al: Expression of recessive alleles by chromosomal mechanisms in retinoblastoma. Nature 305:779-784, 1983
19. Bepler G, Garcia-Blanco M A: Three tumor-suppressor regions on chromosome 11p identified by high-resolution deletion mapping in human non-small-cell lung cancer. Proc Natl Acad Sci USA 91:5513-5517, 1994
20. Fong K M, Zimmerman P V, Smith P J: Correlation of loss of heterozygosity at 11p with tumour progression and survival in non-small cell lung cancer. Genes Chrom Cancer 10:183-189, 1994
21. Zhao B, Bepler G: Transcript map and complete genomic sequence for the 310 kb region of minimal allele loss on chromosome segment 11p15.5 in non-small-cell lung cancer. Oncogene 20:in press, 2001
22. Mountain C: Revisions in the international system for staging lung cancer. Chest 111:1710-1717, 1997
23. Giovino G A, Henningfield J E, Tomar S L, et al: Epidemiology of tobacco use and dependence. Epidemiologic Rev 17:48-65, 1995
24. Rosell R, Pifarre A, Monzo M, et al: Reduced survival in patients with stage-I non-small-cell lung cancer associated with DNA-replication errors. Int J Cancer 74:330-4, 1997
25. Schreiber G, Fong K, Peterson B, et al: Smoking, gender, and survival association with allele loss for the LOH11B lung cancer region on chromosome 11. Cancer Epidemiol Biomarkers Prev 6:315-319, 1997
26. Sanchez-Cespedes M, Rosell R, Pifarre A, et al: Microsatellite alterations at 5q21, 11p13, and 11p15.5 do not predict survival in non-small cell lung cancer. Clin Cancer Res 3:1229-1235, 1997
27. Mitsudomi T, Oyama T, Nishida K, et al: Loss of heterozygosity at 3p in non-small cell lung cancer and its prognostic implication. Clin Cancer Res 2:1185-1189, 1996
28. Geradts J, Fong K, Zimmerman P, et al: Correlation of abnormal R B, p16ink4a, and p53 expression with 3p loss of heterozygosity, other genetic abnormalities, and clinical features in 103 primary non-small cell lung cancers. Clin Cancer Res 5:791-800, 1999
29. Jen J, Kim H, Piantadosi S, et al: Allelic loss of chromosome 18q and prognosis in colorectal cancer. N Engl J Med 331:213-221, 1994

30. Moertel C G, Fleming T R, McDonald J S, et al: Levamisole and fluorouracil for adjuvant therapy of resected colon carcinoma. N Engl J Med 322:352-358, 1990

31. CancerNet: Non-small cell lung cancer treatment—health professionals. National Cancer Institute PDQ: http://cancernet.nci.nih.gov/clinpdq/soa/non-small_cell_lung_cancer physician.html, 1999.

What is claimed is:

1. A method for detecting loss of heterozygosity in chromosome region 11p15.5 in an individual diagnosed with non-small-cell lung cancer (NSCLC) tumor comprising the steps of:
   a) obtaining tissue samples from the NSCLC tumor and from normal tissue;
   b) amplifying DNA in the tissue samples from the NSCLC tumor tissue and the normal tissue with a set of primers selected from the group consisting of: set of forward primer SEQ ID NO:3 and reverse primer SEQ ID NO:4, set of forward primer SEQ ID NO:7 and reverse primer SEQ ID NO:8, and set of forward primer SEQ ID NO:9 and reverse primer SEQ ID NO:10, or combinations thereof;
   c) measuring the amount of amplified products;
   d) comparing the amount of amplified products from the NSCLC tumor tissue with the amount of amplified products from the normal tissue;
   e) identifying the NSCLC tumor tissue as having LOH if the amplified products from the NSCLC tumor tissue are less than the amplified products from the normal tissue.

2. The method of claim 1, wherein the amplification is carried out by polymerase chain reaction.

3. The method of claim 2, wherein the primers are end-labeled.

4. The method of claim 1, wherein the amplified products are measured by using a phosphorimager system.

5. A method for identifying an individual diagnosed with non-small-cell lung cancer (NSCLC) tumor as having a poor prognosis comprising the steps of:
   a) obtaining tissue samples from the NSCLC tumor and from normal tissue of the individual;
   b) amplifying DNA in the tissue samples from the NSCLC tumor and normal tissue with primers to amplify polymorphic markers in chromosome regions 11p15.5, wherein the markers are selected from the group consisting of SSA44C/T, D11S4932, RR19, RR(−)37A/C, RR(−)524C/T and combinations thereof;
   c) comparing the amplified products from the NSCLC tumor tissue and normal tissue;
   d) identifying the NSCLC tumor tissue as having loss of heterozygosity if the amplified products from the NSCLC tumor tissue are less than the amplified products from the normal tissue;
   wherein an identification of a loss of heterozygosity in d) is indicative of a poorer prognosis for the individual relative to an individual diagnosed with NSCLC who does not have a loss of heterozygosity in chromosome region 11p15.5.

6. The method of claim 5, wherein the amplification is carried out by polymerase chain reaction.

7. The method of claim 5, wherein measuring the amount of amplified products comprises using a phosphorimager system.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: artificial
<220> FEATURE:
<221> NAME/KEY:
<222> LOCATION:
<223> OTHER INFORMATION: SSA44C/T Forward Primer [centromeric]

<400> SEQUENCE: 1
cccctttcct ctcagacttg                                                    20

<210> SEQ ID NO 2
<211> LENGTH: 22
<212> TYPE: DNA
<213> ORGANISM: artificial
<220> FEATURE:
<221> NAME/KEY:
<222> LOCATION:
<223> OTHER INFORMATION: SSA44C/T  Reverse Primer [telomeric]

<400> SEQUENCE: 2
atctagtggg gttcactcac ct                                                 22

<210> SEQ ID NO 3
<211> LENGTH: 21
<212> TYPE: DNA
<213> ORGANISM: artificial
<220> FEATURE:
<221> NAME/KEY:
<222> LOCATION:
<223> OTHER INFORMATION: D11S4932 Forward Primer [centromeric]

<400> SEQUENCE: 3
gacaaagcca aagctcttta c                                                  21

<210> SEQ ID NO 4
<211> LENGTH: 21
<212> TYPE: DNA
<213> ORGANISM: artificial
<220> FEATURE:
<221> NAME/KEY:
<222> LOCATION:
<223> OTHER INFORMATION: D11S4932 Reverse Primer [telomeric]

<400> SEQUENCE: 4
ctggaagaca ctttctcaaa c                                                  21

<210> SEQ ID NO 5
<211> LENGTH: 20
<212> TYPE: DNA
<213> ORGANISM: artificial
<220> FEATURE:
<221> NAME/KEY:
<222> LOCATION:
<223> OTHER INFORMATION: RRI9 Forward Primer [centromeric]

<400> SEQUENCE: 5
ccccaaagtc catcagagag                                                    20
```

```
<210> SEQ ID NO 6
<211> LENGTH: 20
<212> TYPE: DNA
<213> ORGANISM: artificial
<220> FEATURE:
<221> NAME/KEY:
<222> LOCATION:
<223> OTHER INFORMATION: RRI9 Reverse Primer [telomeric]

<400> SEQUENCE: 6
tctccctaat tggctggatg                                               20

<210> SEQ ID NO 7
<211> LENGTH: 20
<212> TYPE: DNA
<213> ORGANISM: artificial
<220> FEATURE:
<221> NAME/KEY:
<222> LOCATION:
<223> OTHER INFORMATION: RR(-)37A/C Forward Primer [centromeric]

<400> SEQUENCE: 7
ctgctcaggg gaaagaactg                                               20

<210> SEQ ID NO 8
<211> LENGTH: 20
<212> TYPE: DNA
<213> ORGANISM: artificial
<220> FEATURE:
<221> NAME/KEY:
<222> LOCATION:
<223> OTHER INFORMATION: RR(-)37A/C Reverse Primer [telomeric]

<400> SEQUENCE: 8
ggtcttgccc agactcaaca                                               20

<210> SEQ ID NO 9
<211> LENGTH: 20
<212> TYPE: DNA
<213> ORGANISM: artificial
<220> FEATURE:
<221> NAME/KEY:
<222> LOCATION:
<223> OTHER INFORMATION: RR(-)524C/T Forward Primer [centromeric]

<400> SEQUENCE: 9
cttttagatc ggccagagga                                               20

<210> SEQ ID NO 10
<211> LENGTH: 20
<212> TYPE: DNA
<213> ORGANISM: artificial
<220> FEATURE:
<221> NAME/KEY:
<222> LOCATION:
<223> OTHER INFORMATION: RR(-)524C/T Reverse Primer [telomeric]

<400> SEQUENCE: 10
ataccctgtc tctgccacca                                               20
```